(12) United States Patent
Harms et al.

(10) Patent No.: US 9,078,973 B2
(45) Date of Patent: Jul. 14, 2015

(54) DRUG DELIVERY DEVICE

(75) Inventors: Michael Harms, Frankfurt am Main (DE); Steffen Raab, Frankfurt am Main (DE); Uwe Dasbach, Frankfurt am Main (DE); Udo Stauder, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 382 days.

(21) Appl. No.: 13/258,151

(22) PCT Filed: Mar. 31, 2010

(86) PCT No.: PCT/EP2010/054336
§ 371 (c)(1),
(2), (4) Date: Dec. 30, 2011

(87) PCT Pub. No.: WO2010/112557
PCT Pub. Date: Oct. 7, 2010

(65) Prior Publication Data
US 2012/0095411 A1    Apr. 19, 2012

Related U.S. Application Data

(60) Provisional application No. 61/168,978, filed on Apr. 14, 2009.

(30) Foreign Application Priority Data

Mar. 31, 2009  (EP) .................................... 09004661

(51) Int. Cl.
*A61M 5/31*   (2006.01)
*A61M 5/32*   (2006.01)

(52) U.S. Cl.
CPC ........... *A61M 5/3129* (2013.01); *A61M 5/3135* (2013.01); *A61M 5/321* (2013.01); *A61M 2005/3139* (2013.01)

(58) Field of Classification Search
CPC .... B43K 23/003; A61M 5/3129; A61M 5/24; A61M 5/31511; A61M 2005/3139; A61M 5/3135; A61M 5/31551; A61M 5/3158; A61M 5/31593; A61M 5/31561
USPC .................................................. 604/187, 211
See application file for complete search history.

(56) References Cited

U.S. PATENT DOCUMENTS 1,757,809 A  *  5/1930  Montuori ....................... 604/235
2,857,912 A  *  10/1958  Feinstone et al. ............. 604/192

(Continued)

FOREIGN PATENT DOCUMENTS

| EP | 0777123 | 6/1997 |
| WO | 2006/063015 | 6/2006 |
| WO | 2007/137083 | 11/2007 |
| WO | 2008/003560 | 1/2008 |

OTHER PUBLICATIONS

European Search Report for EP Application No. 09004661 dated Aug. 20, 2009.
International Search Report for International Application No. PCT/EP2010/054336, dated Jul. 12, 2010.
International Preliminary Report on Patentability for International App. No. PCT/EP2010/054336, dated Oct. 4, 2011.

*Primary Examiner* — Bhisma Mehta
*Assistant Examiner* — William Frehe
(74) *Attorney, Agent, or Firm* — McDonnell Boehnen Hulbert & Berghoff LLP (57) ABSTRACT

A drug delivery device comprises an outer housing rollable around a rotation axis and at least one stop member. The stop member protrudes radially from the outer housing of the drug delivery device and is configured to prevent rolling movement of the drug delivery device along a predetermined surface. The outer housing comprises a main housing and a dose member. The dose member is movable with respect to the main housing when setting and/or delivering a dose of a drug. The stop member comprises a first part and a second part, wherein the first part is arranged on the main housing and the second part is arranged on the dose member.

15 Claims, 3 Drawing Sheets

(56) References Cited

U.S. PATENT DOCUMENTS

| | | | |
|---|---|---|---|
| 2,882,901 A * | 4/1959 | De Venezia | 604/227 |
| 2,902,995 A * | 9/1959 | Loper | 604/243 |
| 4,900,309 A * | 2/1990 | Netherton et al. | 336/192 |
| 5,509,903 A * | 4/1996 | Grendahl et al. | 604/187 |
| 5,624,400 A * | 4/1997 | Firth et al. | 604/110 |
| 2004/0165931 A1* | 8/2004 | Cooper et al. | 401/6 |
| 2007/0113861 A1 | 5/2007 | Knudsen et al. | |
| 2008/0228147 A1* | 9/2008 | David-Hegerich et al. | 604/198 |

* cited by examiner

DRUG DELIVERY DEVICE

CROSS REFERENCE TO RELATED APPLICATIONS

The present application is a U.S. National Phase Application pursuant to 35 U.S.C. §371 of International Application No. PCT/EP2010/054336 filed Mar. 31, 2010, which claims priority to European Patent Application No. 09004661.6 filed on Mar. 31, 2009, and also U.S. Provisional Patent Application No. 61/168,978 filed on Apr. 14, 2009. The entire disclosure contents of these applications are herewith incorporated by reference into the present application.

FIELD OF THE INVENTION

This disclosure relates to a drug delivery device.

BACKGROUND

Drug delivery devices may comprise a tubular or cylindrical shape. Hence, they are prone to unintentional rotational movement with respect to a surface onto which they have been placed. Of course, unintentional movement increases the risk of damage to the drug delivery device. For example, the device may roll on a table over the edge of said table, thereby falling on the floor. This may destroy the drug delivery device or seriously damage parts thereof.

SUMMARY

It is an object of the present invention to provide for an improved drug delivery device.

This object is achieved by a drug delivery device according to the independent claim. Further features are subject matters of the dependent claims.

According to one aspect, a drug delivery device is provided which comprises an outer housing rollable around a rotation axis and at least one stop member. The stop member may protrude radially from the outer housing of the drug delivery device. The stop member may be configured to prevent rolling movement of the drug delivery device along a predetermined surface.

The outer housing may be of tubular or cylindrical shape. Due to the tubular or cylindrical shape of the outer housing, the drug delivery device is particularly prone to rolling along a predetermined surface, where it has been placed.

Preferably, the stop member provides for a means for stabilizing the device, i.e. for preventing and/or limiting the rolling of the drug delivery device by acting as a blocking member against unintentional rotational movement of the drug delivery device along the predetermined surface. Hence, the stop member prevents and/or limits the rolling of the drug delivery device along the surface, for example a table. Accordingly, if a user has placed the drug delivery device on the table, the risk of the device rolling along the table can be considerably reduced.

In a preferred embodiment the stop member protrudes radially from the outer housing by at least 0.75 mm.

Preferably, the stop member comprises a height with respect to the outer housing and the height of the stop member is large enough to prevent unintentional rolling movement of the drug delivery device. Preferably, the stop member protrudes from the outer housing in such a way that rolling of the drug delivery device along the predetermined surface is prevented and/or limited even at a certain inclination of the surface or if the surface is exposed to vibrations, which may occur when the user of the drug delivery device is in a train or an aero plane, for example.

In a preferred embodiment, the stop member extends along the rotation axis by 1.0 cm or less.

Preferably, the extension of the stop member along the rotation axis is large enough to effectively prevent rolling of the drug delivery device along the predetermined surface.

According to a further preferred embodiment, the stop member extends along an outer surface of the outer housing and transversally with respect to the rotation axis by 0.5 cm or less.

The outer housing of the drug delivery device comprises an outer surface from which the stop member may protrude. Preferably, the extension of the stop member along said outer surface and transversally with respect to the rotation axis (e.g. the azimuthally extension of the stop member) is suited to effectively prevent unintentional rolling of the drug delivery device.

According to a preferred embodiment, the stop member comprises a surface which faces away from the outer housing of the drug delivery device. This surface may be plane or curved.

Due to a plane shape of the surface of the stop member said surface may serve as a bearing surface for the drug delivery device. Thus, the stop member may be adapted to block rotation and, simultaneously, provide for a bearing surface. A curved surface of the stop member may fit better to a curved enveloping surface of the device than a plane surface.

According to a preferred embodiment, the outer housing comprises a main housing and a dose member. The dose member may be movable with respect to the main housing when setting and/or delivering a dose of a drug. The stop member preferably comprises a first part and a second part, wherein the first part is arranged on the main housing and the second part is arranged on the dose member. Accordingly, the second part is movable with respect to the first part.

Preferably, the dose member of the drug delivery device is axially movable and/or rotatable with respect to the main housing of said device. Hence, the second part of the stop member may be movable and/or rotatable with respect to the first part of the stop member, which is arranged on the main housing.

In a preferred embodiment, the second part of the stop member is configured to continue the shape of the first part and/or to be aligned with the first part of the stop member, in particular, when the dose member is in an initial state before the dose is set.

In the initial state the dose member was not rotated or axially displaced with respect to the main housing for setting of a dose. Consequently, in the initial state of the dose member the first part of the stop member is preferably aligned with the second part of the stop member.

According to a preferred embodiment, the stop member is configured to prevent rolling of the drug delivery device, preferably only, when the second part of said stop member is aligned with the first part of the stop member.

In a preferred embodiment, the drug delivery device, in particular the outer housing, comprises two sections wherein each of the sections has a defined diameter. The diameters of the two sections may be different. The stop member is expediently arranged in that section which comprises the greater diameter.

For effectively preventing unintentional rolling of the drug delivery device along the predetermined surface the stop member is preferably placed in the section comprising the greater diameter, which is that section in which the greatest torque may act against a tendency of rolling.

In a preferred embodiment, the stop member is arranged in a region of a proximal end of the outer housing.

In a preferred embodiment, a cap is removably attachable to the drug delivery device to cover a distal end of said device. The stop member is preferably configured to prevent rolling of the device along the predetermined surface when the cap is detached from the device.

Preferably, the cap comprises a clip which may prevent rolling of the drug delivery device when the cap is attached to the device. Consequently, the stop member prevents unintentional rolling of the drug delivery device (only) if the cap is removed from the device, a situation in which the device is especially prone to rolling due to the lacking clip.

According to a preferred embodiment, the stop member is shaped rib-like, in particular in the initial state of the dose member.

A rib-like shape may be especially suitable to prevent unintentional rolling of the drug delivery device along the predetermined surface.

According to a preferred embodiment, the drug delivery device is a pen-type device.

Pen-type devices are, on account of their elongated shape, particularly prone to unintentional rolling movement.

According to a preferred embodiment, a drug delivery device is provided comprising an outer housing rollable around a rotation axis and at least one stop member, wherein the stop member protrudes radially from the outer housing of the drug delivery device and wherein the stop member is configured to prevent rolling movement of the drug delivery device along a predetermined surface.

BRIEF DESCRIPTION OF THE FIGURES

Further features and refinements become apparent from the following description of the exemplary embodiment in connection with the accompanying figures.

DETAILED DESCRIPTION

Like elements, elements of the same kind and identically acting elements may be provided with the same reference numerals in the figures.

Figure 1:
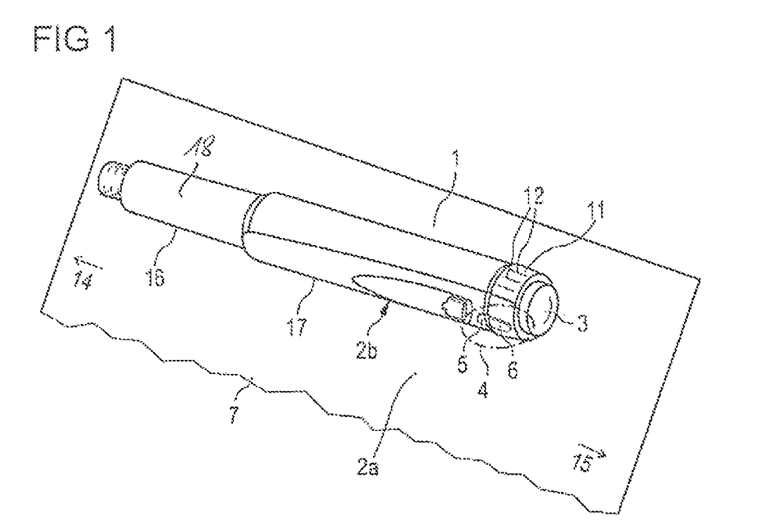
FIG. 1 schematically shows an embodiment of a drug delivery device on the basis of an oblique plan view, FIG. 2 schematically shows a more detailed view of a part of the drug delivery device of FIG. 1 on the basis of a sectional view, FIG. 3 schematically shows an embodiment of a cap on the basis of a sectional view.

Turning to FIG. 1, a drug delivery device 1 comprises an outer housing 2a. The outer housing 2a comprises a main housing 2b and a dose member 3. FIG. 1 further shows a stop member 4 protruding from the outer housing 2a. The stop member 4 comprises a first part 5 and a second part 6. The first part 5 is arranged on the main housing 2b and the second part 6 is arranged on the dose member 3. The drug delivery device 1 comprises two sections 16, 17, a distal end and a proximal end as well as a cartridge holder 18. The device 1 further comprises a rotation axis which extends axially along said drug delivery device 1, in particular along a (main) longitudinal axis thereof. The device 1 is arranged on a (predetermined) surface 7.

The dose member 3 has an outer surface 11 as well as protrusions 12. Protrusions 12 and/or stop member 4 may be oriented in the axial direction. Protrusions 12 may be disposed about a perimeter of dose member 3, in particular surface 11 thereof.

The drug delivery device 1 has a distal end and a proximal end. The distal end is indicated by arrow 14, which refers to that end of the drug delivery device 1 which is closest to a dispensing end of the drug delivery device 1. The proximal end is indicated by arrow 15 referring to that end of the device 1 which is furthest away from the dispensing end of the device 1.

The drug delivery device 1 is a pen-type device, in particular a pen-type injector. The device 1 may be a disposable or a reusable device and may be configured to dispense fixed doses of a drug or variable, preferably user-settable doses of the drug.

The drug delivery device 1 comprises the cartridge holder 18, which may be attached, preferably glued, to the outer housing 2a. The cartridge holder 18 may comprise a cartridge containing a drug. The term "drug" as used herein preferably means a pharmaceutical formulation containing at least one pharmaceutically active compound having a molecular weight up to 1500 Da, or a pharmaceutically active peptide, protein, DNA, RNA, antibody, enzyme, hormone or oligonucleotide, or a mixture thereof, preferably comprising at least one peptide, further preferred a peptide for the treatment of diabetes mellitus or complications associated with diabetes mellitus such as diabetic retinopathy, especially preferred human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin, Lys(B3), Glu(B29) human insulin, Lys(B28), Pro(B29) human insulin, Asp(B28) human insulin, human insulin, wherein proline in position B28 is replaced by Asp, Lys, Leu, Val or Ala and wherein in position B29 Lys may be replaced by Pro, Ala(B26) human insulin, Des(B28-B30) human insulin, Des(B27) human insulin and Des(B30) human insulin.

Insulin derivates are for example B29-N-myristoyl-des (B30) human insulin, B29-N-palmitoyl-des(B30) human insulin, B29-N-myristoyl human insulin, B29-N-palmitoyl human insulin, B28-N-myristoyl LysB28ProB29 human insulin, B28-N-palmitoyl-LysB28ProB29 human insulin, B30-N-myristoyl-ThrB29LysB30 human insulin, B30-N-palmitoyl-ThrB29LysB30 human insulin, B29-N-(N-palmitoyl-Y-glutamyl)-des(B30) human insulin, B29-N-(N-lithocholyl-Y-glutamyl)-des(B30) human insulin, B29-N-(ω-carboxyheptadecanoyl)-des(B30) human insulin and B29-N-(ω-carboxyheptadecanoyl) human insulin.

Exendin-4 preferably means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39), des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(02)25, Asp28] Exendin-4(1-39),
des Pro36 [Met(O)14 Trp(O2)25, IsoAsp28] Exendin-4(1-39), or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
  wherein the group -Lys6-NH2 may be bound to the C-terminus of the Exendin-4 derivative,
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2,
or a pharmaceutically acceptable salt or solvat of any one of the afore-mentioned Exedin-4 derivative.

Hormones are preferably hypophysis hormones or hypothalamus hormones or regulatory active peptides and their antagonists as listed in Rote Liste, ed. 2008, Chapter 50. Examples of hormones are Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. Ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Figure 2:
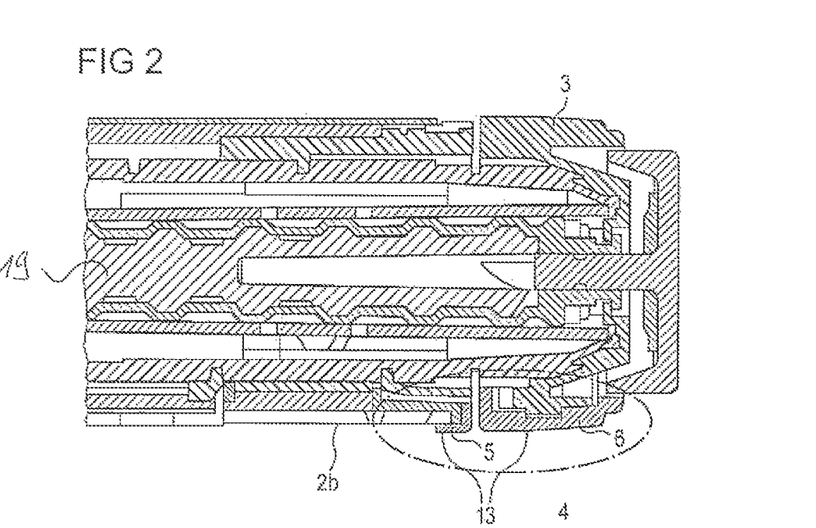

The drug delivery device 1 may further comprise a plunger and a plunger seal (not shown in FIG. 1, see plunger 19 in FIG. 2 which are movable with respect to the outer housing 2a. The plunger 19 may be moved into proximal direction with respect to the outer housing 2a for setting a dose of the drug and the plunger 19 may be moved into distal direction with respect to the outer housing 2a for delivering the dose of the drug. The plunger seal may provide a fluid seal between the cartridge and the plunger 19, which means that the drug cannot move between the cartridge and the plunger 19.

The drug delivery device 1 may further comprise a needle assembly (not shown in FIG. 1), comprising for example a needle mounted to a needle mount, a needle retainer and/or a needle seal. The needle assembly may be attached to the distal end of the cartridge holder 18. Alternatively, the drug delivery device 1 may be a needle-free device.

Figure 4:
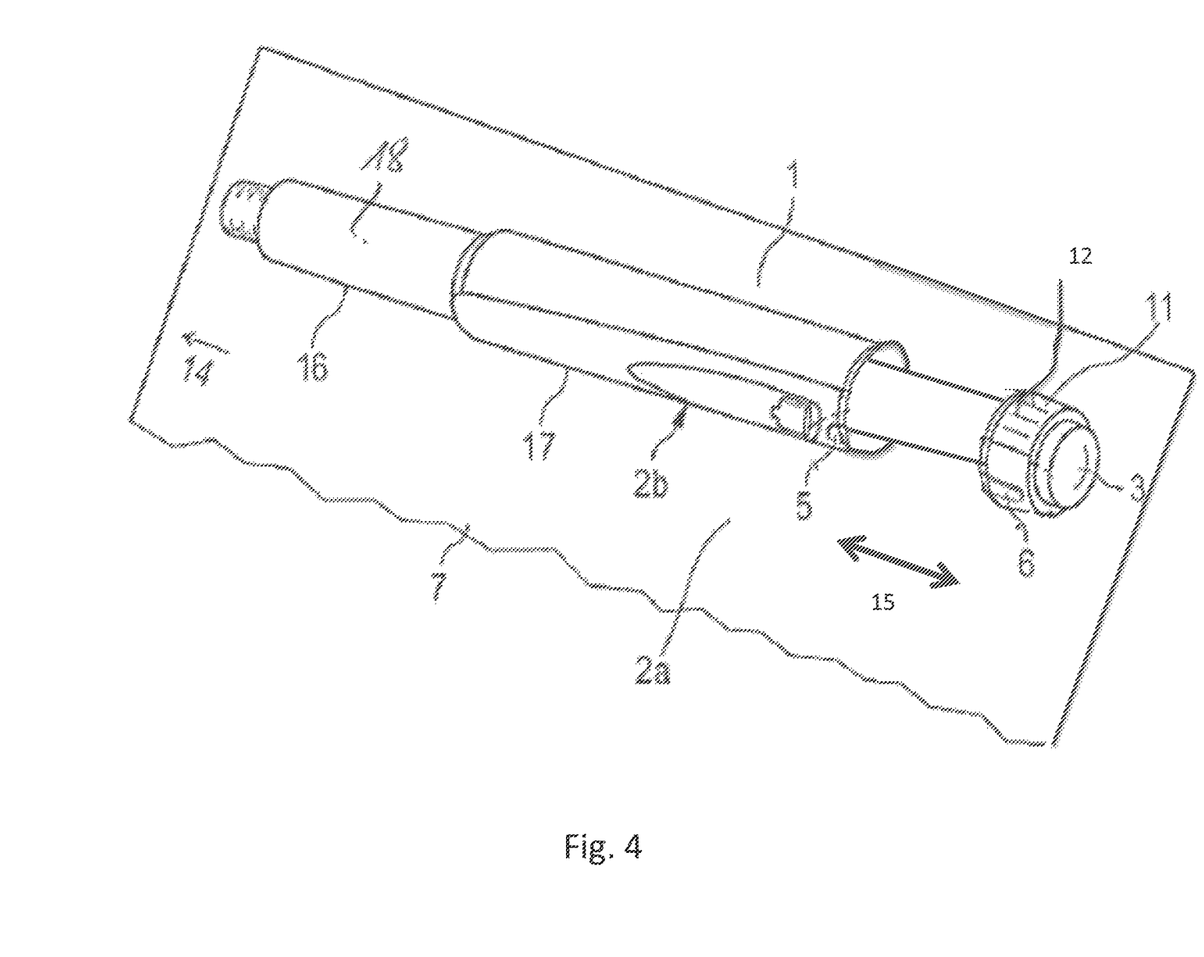
FIG. 4 schematically shows an embodiment of a drug delivery device on the basis of an oblique plan view where the dose member is extended away from the main housing during either dose setting or dose delivery.

The outer housing 2a may be rollable around the rotation axis. The outer housing 2a may comprise a tubular or cylindrical shape, as shown in FIG. 1. The outer housing 2a comprises the main housing 2b, which may be of tubular shape, as indicated in FIG. 1, and the dose member 3. The dose member 3 may further comprise a dose button, which may be depressed by a user for delivering a dose of the drug after the dose has been set. The dose member 3 may be axially displaceable and/or rotatable with respect to the main housing 2b of the drug delivery device 1. Thereby, the dose member 3 may be moved and/or rotated in a proximal direction with respect to the main housing 2b for setting a dose of the drug. Afterwards, the dose member 3 may be moved and/or rotated in a distal direction with respect to the main housing 2b for delivering the previously set dose of the drug. This proximal and distal movement is illustrated by the directional arrow 50 in FIG. 4 that shows the dose member in an extended position away from the main housing. Afterwards, the dose member 3 may be moved and/or rotated in a distal direction with respect to the main housing 2b for delivering the previously set dose of the drug. The dose member 3 is preferably threadedly engaged with the main housing 2b. The distance by which the dose member 3 is displaced in proximal direction with respect to the main housing 2b when setting a dose of the drug may determine the amount of the drug which is dispensed subsequently.

The stop member 4 protrudes radially from the outer housing 2a of the drug delivery device 1, i.e. radially with respect to the rotation axis of the drug delivery device 1. The stop member 4 may be connected to the outer housing 2a. The stop member 4 is configured to prevent and/or to limit an unintentional rolling of the device 1 with respect to the surface 7. The stop member 4 may be configured to permit a certain rolling of the device 1 into a stabilized position of said device 1. Once having rolled into the stabilized position, the drug delivery device 1 is prevented from further rolling along the surface 7 by the stop member 4.

In this embodiment, the drug delivery device 1 comprises two sections 16, 17 each comprising a defined diameter. The section with the greater diameter (in this embodiment section 17) is arranged in the region of the proximal end of the outer housing 2a.

The stop member 4 is arranged in the section 17 comprising the greater diameter, i.e. that section which allows for exerting the greater torque for limiting and/or preventing rolling movement of the drug delivery device 1 via interaction of the stop member 4 and the surface 7. Preferably, the stop member 4 is arranged in the region of the proximal end of the outer housing 2a. For example, the stop member 4 may be shaped rib-like.

The stop member 4 may protrude radially from the outer housing 2a by at least 0.75 mm. Preferably, the stop member 4 protrudes by at least 1.0 mm from the outer housing 2a. The stop member 4 may protrude radially from the outer housing 2a by at least 1.5 mm. Even when the drug delivery device 1 is arranged on an inclined surface 7, a stop member 4 of this kind may still be suitable for preventing rolling movement of the device 1.

In this embodiment the stop member 4 extends along the rotation axis (i.e. the axial extension of the stop member 4) by 1.0 cm or less, preferably by 0.75 cm or less. The stop member 4 extends along an outer surface of the outer housing 2a and transversally with respect to the rotation axis (i.e. the azimuthal extension of the stop member 4) by 0.5 cm or less, preferably by 0.3 cm or less.

Radial protrusion, axial extension and azimuthal extension of the stop member 4 should be suitable to effectively prevent rolling of the drug delivery device 1 along the surface 7 while not changing the design of said device 1, i.e. its outer appearance, too much.

In addition, radial protrusion, axial extension and azimuthal extension of the stop member 4 should be suitable to prevent rolling of the drug delivery device 1 still at a certain inclination of the surface 7. Preferably, the stop member 4 prevents rolling of the drug delivery device 1 along the surface 7 up to an inclination of 10° of the surface 7 with respect to the earth's surface. Additionally or alternatively, stop member 4 should be suitable to prevent rolling of the device 1 when the defined surface 7 moves and/or vibrates, for example when the user of the device 1 is in a train or an aeroplane.

The stop member 4 may comprise a surface, which faces away from the outer housing 2a (see surface 13 in FIG. 2). In one embodiment, said surface 13 of the stop member 4 may be plane. Thereby, the surface 13 may serve as a bearing surface for the drug delivery device 1 when said device 1 is placed on the predetermined surface 7 with surface 13 contacting predetermined surface 7. In addition to its function as a bearing member, the stop member 4 may act, of course, as a blocking/stabilizing member preventing and/or limiting rolling of the drug delivery device 1 along the surface 7, as described previously. This means, that in this embodiment the stop member 4 may cause the drug delivery device 1 to roll and stay in a desired position. Once having rolled into the desired position the stop member 4 prevents further rolling of the device 1 along the surface 7 and the device 1 may stay in the stable position with bearing surface 13 facing predetermined surface 7.

In another embodiment the surface 13 of the stop member may be curved.

In the shown embodiment, the stop member 4 comprises the first part 5 and the second part 6. The first part is provided on, i.e. protrudes radially from, the main housing 2b. The second part 6 is provided on the dose member 3, i.e. radially protrudes from the dose member 3. Thus, the second part 6 is movable and/or rotatable with respect to the first part 5 of the stop member 4.

Preferably, the dose member 3 comprises an initial state, in which the dose member 3 is not rotated with respect to the main housing 2b (i.e. that state the dose member 3 is in before a dose of the drug is set). Hence, in the initial state of the dose member 3, the second part 6 of the stop member 4 is not rotated with respect to the first part 5 of the stop member.

In the initial state of the dose member 3, the second part 6 of the stop member 4 continues the first part 5 of the stop member 4, e.g. elongates the first part 5 of the stop member 4. Thus, the second part 6 of the stop member 4 is aligned with the first part 5 of the stop member 4. Preferably, the stop member 4 prevents unintentional rolling of the drug delivery device 1 only when the second part 6 of the stop member 4 is aligned with the first part 5 of the stop member, i.e. when the dose member 3 is in the initial state.

The drug delivery device 1 may further comprise a cap (see cap 8 in FIG. 3) covering the distal end of the drug delivery device 1. Said cap 8 may be removably attachable to the drug delivery device 1, e.g. removably attachable to the outer housing 2a of the drug delivery device 1. The cap 8 may be configured to cover the previously mentioned needle assembly (not shown in FIG. 1) of the drug delivery device 1. The cap 8 may prevent said needle assembly from being damaged and/or from being polluted. If attached to the device 1 the cap 8 may be non-rotatable with respect to the outer housing 2a. For removing the cap 8 from the outer housing 2a a user axially moves said cap 8 in distal direction with respect to the outer housing 2a and for attaching the cap 8 onto the outer housing 2a the user may axially move the cap 8 in proximal direction with respect to the outer housing 2a. The cap 8 may be attachable to the outer housing 2a by means of engagement features for example. When attached to the device 1, the cap 8 may be rotationally locked with respect to the drug delivery device 1. Preferably, the cap 8 comprises a clip (see clip 10 in FIG. 3), wherein said clip 10 protrudes from the cap 8 and said clip 10 may be suitable to prevent rolling movement of the drug delivery device 1.

Figure 3:
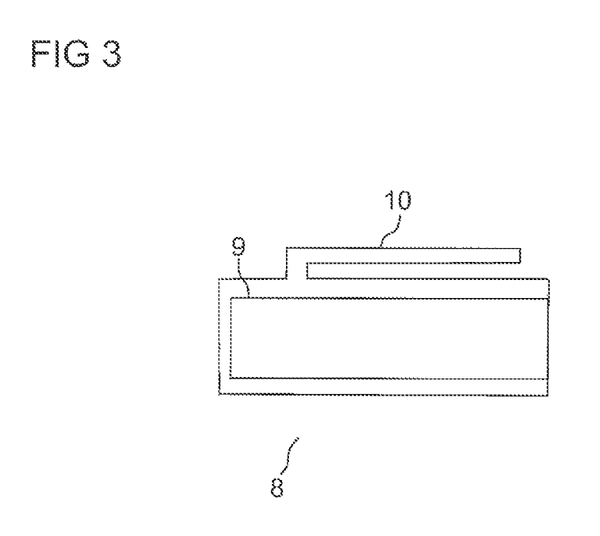

Preferably, the stop member 4 is configured to prevent rolling of the device 1 along the predetermined surface 7 only when the cap 8 and, hence, also clip 10 is detached from the device. When the cap 8 and, consequently the clip 10, have been removed, the drug delivery device 1 may be especially prone to an unintentional rolling with respect to the predetermined surface 7. In particular, unintentional movement without cap 8 is dangerous, as a needle might be relatively unprotected and the risk of accidental piercing of the user is increased. Hence, the stop member 4 is particularly advantageous to prevent and/or to limit rolling of the device 1 when the cap 8 is detached from the drug delivery device 1.

In this embodiment, the dose member 3 comprises the protrusions 12, for example ribs, which protrude radially from the outer surface 11 of said dose member 3. The protrusions 12 may assist a user to grab the dose member 3 and to move and/or rotate the dose member 3 with respect to the main housing 2b for setting and/or delivering a dose of the drug.

Preferably, the protrusions 12 are oriented along the rotation axis of the drug delivery device 1. The protrusions 12 protrude from the outer surface 11 of the dose member 3 up to a defined height. Thereby, the defined height may vary for different protrusions 12. The defined height may amount to a height of up to 0.5 mm with respect to the outer surface 12 of the dose member 3.

The stop member 4 protrudes further radially from the outer housing 2a, i.e. the second part 6 of the stop member 4 protrudes further from the dose member 3 and the first part 5 of the stop member 4 protrudes further from the main housing 2b, than the protrusions 12 protrude from the outer surface 11 of the dose member 3. Preferably, the stop member 4 protrudes radially from the outer housing 2a by at least 1.0 mm (i.e. the second part 6 of the stop member 4 protrudes radially from the dose member 3 by at least 1.0 mm and the first part 5 of the stop member 4 protrudes radially from the main housing 2b by at least 1.0 mm, whereas, preferably, the second part 6 and the first part 5 protrude by an equal distance from the outer housing 2a).

FIG. 2 schematically shows a more detailed view of a part of the drug delivery device of FIG. 1 on the basis of a sectional view.

FIG. 2 shows the proximal end of the drug delivery device 1 of FIG. 1 in a more detailed view, comprising a proximal end side view of the main housing 2b, further comprising the dose member 3 and the stop member 4, which is encircled and which comprises the first part 5 and the second part 6. FIG. 2 further shows a surface 13 of the stop member 4, wherein the surface 13 faces away from the outer housing 2a of the drug delivery device 1, i.e. the surface 13 faces away from the dose member 3 and the main housing 2b.

FIG. 2 shows essentially the same as FIG. 1. In particular, FIG. 2 shows the dose member 3 in the initial state. Thereby, the second part 6 of the stop member 4 is aligned with the first part 5 of the stop member 4. The second part 6 continues the first part 5 of the stop member 4. This enhances the ability of the stop member 4 to stabilize the device 1 against rolling movement with respect to the surface 7. Preferably, the stop member 4 prevents rolling of the device 1 only if the second part 6 of the stop member 4 is aligned with the first part 5 of the stop member 4.

In FIG. 2, the second part 6 of the stop member 4 comprises an axial extension greater than the first part 5 of the stop member 4. Alternatively, the first part 5 may comprise an axial extension greater than the second part 6 or may have an axial extension equal to that of the second part 6. The total axial extension of the first part 5 and the second part 6 of the stop member 4, i.e. the total axial extension of the stop member 4, may amount to a maximum size of 1.0 cm, as explained in connection with FIG. 1, and should be suitable to prevent rolling of the device 1 along the predetermined surface 7 even at a certain inclination of the surface 7. The same values for the radial protrusion, the axial and the azimuthal extension of the stop member 4 apply as mentioned in connection with FIG. 1.

FIG. 3 schematically shows an embodiment of a cap on the basis of a sectional view.

FIG. 3 shows a cap 8 comprising a main body 9 and a clip 10. In addition, FIG. 3 shows plunger 19. Plunger 19 can move with respect to the outer housing 2a as already explained in connection with the description of FIG. 1.

The cap 8 may be removably attachable to the previously described drug delivery device 1 (not shown in FIG. 3) covering the distal end of said drug delivery device 1. The cap 8 may be rotationally locked with respect to the outer housing 2a of the drug delivery device 1 when attached to the drug delivery device 1.

The cap 8 comprises the clip 10 extending axially along the cap 8. The clip 10 may comprise a flexible part so that the clip 10 may be bowed radially outwardly. A user may attach the drug delivery device 1 by means of said clip 10 for example to a pocket for storing and/or transporting said device 1, like a jacket pocket, for example.

The clip 10 protrudes from a main body 9 of the cap 8. Thereby, the clip 10 may be integrally formed with the main body 9 or may be a separate member connected to the main body 9.

The clip 10 protrudes further radially from the main body 9 of the cap 8 than the stop member 4 protrudes radially from the outer surface 2a of the drug delivery device 1. Hence, the clip 10 may serve as a blocking element preventing rolling of the previously described drug delivery device 1 along the surface 7 (not shown in FIG. 3) when attached to the device 1. Consequently, when the cap 8 and hence the clip 10, have been detached from the device 1, the drug delivery device 1 may be especially prone to unintentional rolling with respect to the predetermined surface 7. Hence, the stop member 4 preferably prevents and/or limits rolling of the device 1 only when the cap 8 is detached from the drug delivery device 1.

Other implementations are within the scope of the following claims. Elements of different implementations may be combined to form implementations not specifically described herein.

The invention claimed is:

1. A drug delivery device, comprising
an outer housing rollable around a rotation axis and at least one stop member, wherein the stop member protrudes radially from the outer housing of the drug delivery device and wherein the stop member is configured to prevent rolling movement of the drug delivery device along a predetermined surface, wherein the outer housing comprises a main housing and a dose member, wherein the dose member is configured to abut the main housing in an initial state and to move proximally a distance away from the main housing to set a dose and then to move distally to deliver the set dose and wherein the stop member comprises a first part and a second part, wherein the first part is arranged on the main housing and the second part is arranged on the dose member such that during dose setting the second part moves proximally relative to the first part and wherein the second part is aligned with the first part so that the second part is configured to continue a shape of the first part of the stop member when the dose member is in an initial state before the dose is set.

2. The drug delivery device according to claim 1, wherein the stop member protrudes radially from the outer housing by at least 0.75 mm.

3. The drug delivery device according to claim 1, wherein the stop member extends along the rotation axis by 1.0 cm or less.

4. The drug delivery device according to claim 1, wherein the stop member extends along an outer surface of the outer housing and transversally with respect to the rotation axis by 0.5 cm or less.

5. The drug delivery device according to claim 1, wherein the stop member comprises a surface which faces away from the outer housing of the drug delivery device and wherein said surface is plane.

6. The drug delivery device according to claim 1, wherein the stop member comprises a surface which faces away from the outer housing of the drug delivery device and wherein said surface is curved.

7. The drug delivery device according to claim 1, wherein the stop member is configured to prevent rolling of the drug delivery device when the second part of said stop member is aligned with the first part of the stop member.

8. The drug delivery device according to claim 1, wherein the dose member comprises, in addition to the second part of the stop member, a defined number of protrusions, wherein said protrusions protrude radially from an outer surface of said dose member and wherein the stop member protrudes further from the outer housing in the radial direction than any of the protrusions protrudes from the dose member in the radial direction.

9. The drug delivery device according to claim 1, wherein the drug delivery device comprises two sections, wherein each of the sections has a defined diameter, and wherein the stop member is arranged in that section which has the greater diameter.

10. The drug delivery device according to claim 1, wherein the stop member is arranged in a region of a proximal end of the outer housing.

11. The drug delivery device according to claim 1, wherein a cap is removably attachable to the drug delivery device to cover a distal end of said device and wherein the stop member is configured to prevent rolling of the device along the predetermined surface when the cap is detached from the device.

12. The drug delivery device according to claim 1, wherein the stop member is shaped rib-like.

13. The drug delivery device according to claim 1, wherein the drug delivery device is a pen-type device.

14. The drug delivery device according to claim 1 comprising a cartridge holder which comprises a cartridge containing a drug.

15. A drug delivery device, comprising
an outer housing rollable around a rotation axis and at least one stop member, wherein the stop member protrudes radially from the outer housing of the drug delivery device and wherein the stop member is configured to prevent rolling movement of the drug delivery device along a predetermined surface, wherein the outer housing comprises a main housing and a dose member, wherein the dose member is configured to move proximally a distance away from the main housing to set a dose and then to move distally to deliver the set dose and wherein the stop member comprises a first part and a second part, wherein the first part is arranged on the main housing and the second part is arranged on the dose member such that during dose setting the second part moves proximally relative to the first part and wherein the second part is aligned with the first part so that the second part is configured to continue a shape of the first part of the stop member when the dose member is in an initial state before the dose is set.

* * * * *